(12) United States Patent
Hodosh

(10) Patent No.: US 6,524,623 B1
(45) Date of Patent: Feb. 25, 2003

(54) THERAPEUTIC COMPOSITIONS AND METHODS OF USE THEREOF

(76) Inventor: Milton Hodosh, 243 Elmwood Ave., Providence, RI (US) 02907

( * ) Notice: Subject to any disclaimer, the term of this patent is extended or adjusted under 35 U.S.C. 154(b) by 0 days.

(21) Appl. No.: 09/633,424

(22) Filed: Aug. 7, 2000

Related U.S. Application Data

(63) Continuation-in-part of application No. 09/439,858, filed on Nov. 12, 1999, now Pat. No. 6,099,868.

(51) Int. Cl.[7] ............... A61K 33/00; A61K 31/56; A61K 31/34; A61K 31/24; A61K 31/19; A61K 31/195

(52) U.S. Cl. ............... 424/600; 514/178; 514/470; 514/535; 514/557; 514/561

(58) Field of Search ............ 424/600; 514/178, 514/470, 535, 557, 561

(56) References Cited

U.S. PATENT DOCUMENTS

| | | | |
|---|---|---|---|
| 3,863,006 A | | 1/1975 | Hodosh |
| 4,060,600 A | | 11/1977 | Vit |
| 4,082,881 A | * | 4/1978 | Chen et al. .......... 424/241 |
| 4,191,750 A | | 3/1980 | Hodosh |
| 4,228,162 A | * | 10/1980 | Luzzi et al. .......... 424/232 |
| 4,343,608 A | | 8/1982 | Hodosh |
| 4,400,373 A | | 8/1983 | Hodosh |
| 4,407,675 A | | 10/1983 | Hodosh |
| 4,525,343 A | | 6/1985 | Raaf |
| 4,585,649 A | | 4/1986 | Lynch |
| 4,610,871 A | | 9/1986 | Lynch |
| 4,610,872 A | | 9/1986 | Lynch |
| 4,627,974 A | | 12/1986 | Lynch |
| 4,627,975 A | | 12/1986 | Lynch |
| 4,627,976 A | | 12/1986 | Lynch |
| 4,627,978 A | | 12/1986 | Lynch |
| 4,627,979 A | | 12/1986 | Lynch |
| 4,627,980 A | | 12/1986 | Lynch |
| 4,632,937 A | | 12/1986 | Lynch |
| 4,711,904 A | * | 12/1987 | Luzzi et al. .......... 514/464 |
| 4,770,871 A | | 9/1988 | Greenshields |
| 4,866,048 A | | 9/1989 | Calverley et al. |
| 4,961,923 A | | 10/1990 | Heyde |
| 5,015,466 A | * | 5/1991 | Parran, Jr. et al. .......... 424/52 |
| 5,032,388 A | | 7/1991 | Tikkanen |
| 5,120,460 A | | 6/1992 | Asai et al. |
| 5,139,768 A | | 8/1992 | Friedman |
| 5,147,632 A | | 9/1992 | Pan et al. |
| 5,153,006 A | | 10/1992 | Hodosh |
| 5,374,417 A | | 12/1994 | Norfleet et al. |
| 5,403,577 A | | 4/1995 | Friedman |
| 5,522,726 A | | 6/1996 | Hodosh |
| 6,099,868 A | * | 8/2000 | Hodosh .......... 424/600 |

OTHER PUBLICATIONS

Physical Pharmacy, Martin et al. (eds), 2nd edition, published 1969 by Lea & Febiger (PA), pp. 175–176.*

* cited by examiner

*Primary Examiner*—Raymond Henley, III
(74) *Attorney, Agent, or Firm*—Salter & Michaelson

(57) ABSTRACT

A therapeutic composition and a method of using the composition are provided. The composition includes an osmotic agent and an active agent. The osmotic agent improves the delivery of the active agent to the targeted tissue site.

35 Claims, No Drawings

THERAPEUTIC COMPOSITIONS AND METHODS OF USE THEREOF

CROSS REFERENCE TO RELATED APPLICATIONS

This application is a continuation-in-part under 35 U.S.C. §120 to commonly owned U.S. patent application Ser. No. 09/439,858, filed Nov. 12, 1999 now U.S. Pat. No. 6,099,868.

BACKGROUND

1. Field of the Invention

The present application is directed to therapeutic compositions including an osmotic agent and an active agent and, in particular, to compositions including dimethyl isosorbide as the osmotic agent.

2. Related Art

Cells and other membranous tissues contain and are surrounded by various fluids that contain electrolytes. The difference in the type and concentration of the electrolytes contained in the cells and membranous tissues may in some instances polarize, or provide an electrical potential across the membrane. For example, in general, the electrolytic fluid contained in the interior of a cell contains more negatively charged ions than the electrolytic fluid surrounding the exterior of the cells, which contains positively charged ions. Thus, it can be seen that the normal state of cells is one in which the electrical charge of the fluids contained in and surround a cell are not balanced. The normal charge difference across the membrane creates an electrical potential which is known as the resting threshold potential. For a nerve to conduct a pain impulse, it must be at its resting threshold potential.

With respect to nerve cells, the electrolytic fluid in the interior of a nerve cell at rest has a resting threshold potential of about −85 millivolts with respect to the electrolytic fluid surrounding the nerve cell. Pain is felt by a subject when an irritant to the nerve cell occurs, causing sodium channels in the nerve cell membrane to open for a brief period of time (on the order of milliseconds), allowing sodium ions contained in the fluid surrounding the nerve cells to move into the fluid contained in the interior of the nerve cells, after which conduction along the nerve takes place, leading to a complete action potential and pain emission.

One example of such a mechanism involves the pulpal nerves. The electrolytic fluid in the interior of the pulpal nerves has a resting threshold potential of about −85 millivolts with respect to the electrolytic fluid surrounding the pulpal nerve cell. When an irritant of about +15 millivolts occurs, sodium ions in the fluid surrounding the pulpal nerve move across the pulpal nerve membrane to the interior of the pulpal nerve and conduction takes place, leading to a complete action potential and pain emission.

One known mechanism for preventing pain in pulpal nerves is to increase the concentration of potassium ions in the electrolytic fluid surrounding the pulpal nerves. Surrounding the pulpal nerves with a high concentration of potassium ions causes the nerve to depolarize. "Depolarization" occurs when the resting threshold potential is increased. In the present instance, the resting threshold potential is increased from −85 millivolts to zero or a positive value. When the resting threshold potential is zero, or a positive value, the nerve cannot initiate a pain impulse. Thus, it is known that if the resting threshold potential of a nerve is increased, it is possible to prevent an action potential from taking place, the nerve will be unable to conduct an impulse, and the subject will not feel pain.

In theory, pain inhibition in the pulpal nerves may be accomplished by a varoety of mechanisms. However, in practice, anatomical constrictions, irregularities, and other resistances ound in the dentinal tubles sometim potassium ions from reaching the electrolytic fluid surrounding the nerve cell.

Any mechanism for charging the resting threshold potential of nerves is desirable for interfering with its ability to illicit pain.

SUMMARY

The present invention is directed, in one embodiment, to a method of decreasing the volume of a cell having a membrane and an electrical potential across the membrane that is substantially equal to a resting threshold potential. The method involves the steps of topically applying a composition containing an osmotic agent, increasing the electrical potential across the cell membrane to a level greater than the resting threshold potential, and decreasing the electrical potential across the cell membrane to a level less than the resting threshold potential.

In another embodiment, the invention is directed to a therapeutic composition. The therapeutic composition includes dimethyl isosorbide and an active agent.

Another embodiment of the present invention is directed to a method of treating a subject. The method involves topically applying an effective amount of a composition containing an osmotic agent and an active agent to an area to be treated.

Another embodiment of the present invention is directed to a method of treating a subject. The method involves topically applying an effective amount of a composition containing dimethyl isosorbide and an active agent to an area to be treated.

DETAILED DESCRIPTION OF THE PREFERRED EMBODIMENTS

The present invention is directed to therapeutic compositions containing at least one osmotic agent and at least one active agent. The compositions may be used topically by subjects to treat, relieve, or treat and relieve, the symptoms of various conditions and disorders, by providing improved delivery of the active agent contained in the composition to the region of interest. The amount of the osmotic agent, the amount of the active agent, or the amount of both the osmotic agent and the active agent contained in the present compositions may be varied in order to achieve the desired therapeutic results. This may be easily accomplished by those of skill in the art using routine experimentation and traditional techniques.

In practice, anatomical constrictions, irregularities, and resistances may sometimes minimize or prevent active agents from reaching a targeted site selected for therapeutic treatment. "Osmotic agent," as used herein, means any agent that raises the osmotic pressure of fluid on one side of a membranous structure drawing water across the membrane, causing the structure to shrink in volume. Using the example of a cell, an osmotic agent according to the present compositions may draw water from the interior of the cell such that the volume of the cell is reduced. When cells in a targeted region are reduced in volume, the intercellular spaces are increased. Thus, the osmotic agents of the present compositions increase the amount of space available between cells, allowing the electrolytic fluid surrounding the cells to move more freely and quickly between the cells.

In addition to increasing the intercellular volume, the reduction in cell volume resulting from the osmotic agents disturbs the normal function of the cells, i.e., the cell with reduced volume is unable to function normally. The functions of nerves that may be disturbed as a result of the cell volume reduction may include the ability to stimulate an inflammatory response and the ability to illicit pain, depending on whether the nerves are from the central nervous system or the autonomic nervous system.

The present compositions unexpectedly allow active agents to be delivered directly to deeper targeted sites, eliminating the need for injections, or systemic (oral) medications that may present safety concerns. The present compositions have the capability to readily penetrate into and through the skin, and in some instances into the underlying tissue. In this manner, the osmotic agent of the present compositions increases the absorption and penetration depth of the active agents into, for example, the skin and underlying tissues, the mucosae, and teeth. Thus, the therapeutic effectiveness of the active agent may be increased for its desired purpose. The increased therapeutic effectiveness of active agents in the present compositions, without untoward side effects, is unexpected.

As a result, many otherwise suitable active agents may be made therapeutically effective by the addition of an osmotic agent to a composition containing an active agent. For example, many active agents have been used to treat diseases or conditions unsuccessfully. In some instances, they have been unsuccessful because the delivery agent involves other tissues and systems (digestive, absorptive, vascular) that are not affected by the disease or conditions, which is generally undesirable. Thus, the active agents are made therapeutically effective with the addition of osmotic agent (tissue healing, pain elimination, etc.) because other systems are not involved and it targets the affected tissues, penetrating them directly.

It is thought that the beneficial effects and therapeutic effectiveness of many active agents are enhanced by the addition of the osmotic agent apparently without entering the deeper pharmokinetic pathways, such as the vascular system, the gastro-intestinal system, or the endocrine system. Therefore, treatment with the present compositions does not involve healthy tissue and eliminates the possibility of side effects, making each substance more effective as a disease fighter, without hazards and side effects.

Suitable osmotic agents that may be used in the present compositions include any agent that raises the osmotic pressure of fluid on one side of a membranous structure and draws water across the membrane, causing the structure giving up the water to shrink in volume. One preferred osmotic agent is dimethyl isosorbide (DMI). While not wishing to be bound to any theory, it is thought that the methyl groups of DMI make it more lipid soluble and increases its capability of being able to pass through membranes in comparison to isosorbide, allowing DMI to cross barriers such as skin or tissue membranes more easily and quickly, much like DMSO. DMI's ability to penetrate barriers provides enhanced penetration and/or absorption of the active agents to the targeted treatment site. Thus, DMI acts as a delivery vehicle for active agents that might otherwise require injection, and this is accomplished without involving other tissues or systems.

The possibilities are enormous as differing beneficial agents for varying treatment regimes can be delivered into targeted sites attacking the problem directly. DMI by virtue of its osmotic penetrating synergizing quality opens a direct route of drug administration enabling targeted therapy that is non-invasive. It encourages patient compliance, and is well tolerated. "Active agent," as used herein, means any beneficial substance including medications, minerals, potassium compounds, corticosteroid, antibiotics, antihistamines, anti-inflammatories, ansaids, nutrients, chemotherapeutic agents, vitamins, and combinations thereof.

Suitable active agents that may be responsive to the synergistic effect of osmotic agent include anti-inflammatories; dentifrices; desensitizing agents; pain relievers; anti-fungal agents; topical anesthetics, e.g: benzocaine, tetracaine, benadryl, etc.; moisturizers; humectants; anti-wrinkle or anti-aging preparations; skin pigment removers; skin cleansers (colds creams); skin peels (e.g. Alpha hydroxy, citric acids, ascorbic acid, retinyl palmitate); antibacterials, e.g.: chlorhexadine, etc., for oral rinses and dermatological usage. The may also be used to treat and prevent periodontal disease being brought by the osmotic into the gingival tissues; sun tanning and blocking preparations (e.g. PABA); sterilizing agents (e.g. alcohol); anti-itch preparations (calamine lotion); topical antibiotics (e.g. Bacitracin, Neosporin); nutrients; preparations that contain sunflower seed oil, nutrients and other agents (e.g. mucopolysaccharides, wheat protein, wheat amino acids, yeast extract, cysteine, methionine, glutamine, biotin, niacin, tocopherol, lineic acid, arochidoric acid, saw palmetto extract, methyl nicotinate, ginseng extract, inositol, tetrasodium EDTA); agents that improve hair health and growth; balms used to relive muscle pain (e.g. camphor, menthol, salicylate (menthol, trolanne), capsacin); and, pain relieving hemorrhoid preparations (e.g. Preparation-H), antihistamines, ansaids, chemotherapeutic agents, vitamins, corticosteroid, antibiotics, potassium compounds, minerals, and other beneficial substances.

Thus, the present compositions containing osmotic agent and an active agent have increased therapeutic effectiveness in comparison to compositions without the osmotic agent.

Increasing the concentration of the osmotic agent in the electrolytic fluid surrounding a cell increases the osmotic pressure of the electrolytic fluid surrounding the cell. An increase in the osmotic pressure in the electrolytic fluid surrounding the cell causes water to be drawn from the interior of the cell, resulting in a reduction in cell volume (cell shrinkage).

In order to regain equilibrium, the cell must restore its lost volume. Potassium ion influx is necessary to restore cell volume. Cell and membranous tissue shrinkage provides a strong stimulus for the uptake of potassium across the cell membrane, into the interior of the nerve cell, resulting in an increased concentration of potassium ions in the electrolytic fluid contained in the cell.

In order to regain equilibrium, the potassium ions contained in the electrolytic fluid contained in the interior of the cell will escape and cross the cell membrane into the electrolytic fluid surrounding the cell. When this occurs, the electrical potential across the cell membrane is increased, resulting in a potential that is more highly negative than the resting threshold potential, typically on the order of about −110 millivolts. Because a nerve cell must be at its resting threshold potential in order to form an action potential for the conduction of pain, the increased negative potential (hyperpolarity) across the cell membrane prevents this from occurring. Moreover, the potassium ions in the electrolytic fluid that surrounds the nerve cell slows the escape of potassium ions from the electrolytic fluid contained within the cell, further delaying the cell's return to its normal volume and normal resting threshold potential (−85 mvs.) To conduct an impulse, the nerve must be at the normal resting threshold potential. Thus, the nerve cannot conduct an impulse.

The compositions described above are administered in effective amounts. An effective amount is a dosage of the composition sufficient to provide a medically desirably result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, an effective amount for treating psoriasis would be an amount sufficient to slow or halt the development or further progression of psoriatic lesions. It is preferred generally that a maximum dose be used, that is, the highest safe dose according to sound medical judgment.

It is expected that the compositions may be applied in one or several administrations per day, preferably topically. In the event that a response in the subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrocholoric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compositions may be combined, optionally, with a pharmaceutically-acceptable carrier. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active agent is combined to facilitate the application. The components of the osmotic agents and the active agents also are capable of being co-mingled with such carriers, other additives, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal. The compositions may also include a variety of other materials such as solvents, surfactants, thickeners, colorants, flavorants, and the like.

A variety of administration routes are available. The particular mode selected will depend of course, upon the particular active agent selected, the severity of the condition being treated and the dosage required for therapeutic efficacy. The methods of the invention, generally speaking, may be practiced using any mode of administration that is medically acceptable, meaning any mode that produces effective levels of the active agents without causing clinically unacceptable adverse effects. According to one particular characteristic of the invention, these products are used for the preparation of a pharmaceutical composition intended for local topical application, and may be in any suitable form including liquids, pastes, creams, ointments, gels, lotions, chewing gum, or any other form desired. The pharmaceutical composition may also be in the form of a liquid, soft capsules, solution, or transdermal patches containing the active agent. Such modes of administration include topical routes.

The pharmaceutical compositions may conveniently be presented in unit dosage form and may be prepared by any of the methods well known in the art of pharmacy. All methods may include the step of bringing the active agents and osmotic agents into association with a carrier which constitutes one or more accessory ingredients. In general, the compositions may be prepared by uniformly and intimately bringing the active agents into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active agents. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the active agents described above, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like.

Use of a long-term sustained release implant may be particularly suitable for treatment of chronic conditions. Long-term release, are used herein, means that the implant is constructed and arranged to deliver therapeutic levels of the active agent for at least 30 days, and preferably 60 days. Long-term sustained release implants are well-known to those of ordinary skill in the art and include some of the release systems described above.

In some embodiments of the present composition, the active agent may be a pain reliever or desensitizer. "Pain reliever," as used herein, means an active agent that reduces or eliminates a subject's pain. "Desensitizer," as used herein, means an active agent that reduces or eliminates a subject's sensitivity to a sensitizing agent or to a sensitive area of the subject's body. One preferred composition includes potassium ions, from potassium nitrate, as a pain reliever and/or a desensitizer. Potassium ions from a potassium nitrate source are known to desensitize hypersensitive teeth by nerve depolarization. Potassium nitrate travels through the dentinal tubules and causes the pulpal nerves to depolarize by bathing them with potassium ions. The relatively high concentration of potassium ions contained in the electrolytic fluid surrounding the pulpal nerves changes the resting threshold potential of the pulpal nerve from −85 millivolts to zero or a positive value and prevents initiation of an action potential. This inhibits nerve conductance and pain emission, and in this way it desensitizes hypersensitive teeth.

A composition containing an osmotic agent and potassium nitrate is able to reduce the cell volume, increase the intercellular openings and increase the amount of potassium ions that may be delivered to the pulpal nerve in comparison to a composition without the osmotic agent.

The increased intercellular volume resulting from the osmotic agent allows the composition including potassium nitrate to overcome the resistant factors of the dentin/pulp barriers and to more rapidly reach the pulpal nerves, blood vessels, and embryonic connection tissues. It overcomes the tubular constrictions, irregularities, man-made tubular obliterations, dentinal sclerosis, odontoblast processes, fluid with contained minerals and immunoglobulins, tubule contained bacteria, antibiotics, anti-microbial agents, odontoblasts, odontoblast junctions (tight, intermediate, and gap), and intercellular bridges that restrict and slow the penetration of potassium ions into pulpal tissues. As the osmotic agent advances through the dentinal tubules, it encounters the previously mentioned structures. Due to its osmotic qualities, the osmotic agent opens intercellular spaces between cells as well as spaces through cells. The intercellular bridges connecting cells (odontoblasts) serve as permeability barriers.

The present compositions can then flow through the bridge spaces, junctions, and enlarged openings between the shrunken odontoblasts processes and odontoblasts, enhancing the permeability of the dentin/pulp. The fluid containing the potassium ions then flows more rapidly and easily through the newly created spaces to reach the pulpal nerves and blood vessels.

In a similar manner, pulpal nerves lose water and shrink significantly due to the increased osmotic pressure caused by the surrounding fluid containing potassium nitrate and osmotic agent. When cells and membranous structures are caused to shrink osmotically, potassium located outside the nerves' membrane, as well as potassium from the high potassium gradient obtained from the potassium nitrate desensitizer, flows into these nerve cells in quantity. Osmotic cell shrinkage is a strong stimulus for the uptake of potassium. As the captured potassium leaves the inside of nerves, it escapes, leaving a strongly negative hyperpolarized nerve that cannot form an action potential. This dynamic process inhibits pain production and conduction.

Thus, desensitization of hypersensitive teeth may be accomplished by simultaneously depolarizing and hyperpolarizing the pulpal nerves. The osmotic agent DMI works with $KNO_3$ to disturb the functions of the nerve cell simultaneously depolarizing and hyperpolarizing it. These agents antagonize the recovery process to the resting potential. Potassium positioned on the outside of the nerve keeps it depolarized. This slows the escape of the potassium held between the nerve's membranes and makes it more difficult for the nerve to recover volume after shrinking. A lot of potassium outside the nerve keeps the cell shrunken and the nerve so shrunken, is not going to work well. This keeps the nerves inactive longer and causes a faster, more complete, and longer lasting desensitization to take place than potassium nitrate alone that bathes the outside of the pulpal nerves only.

An application of potassium nitrate/osmotic agent desensitizer continues to desensitize for hours after its initial application because the composition accomplishes desensitization without obliterating or diminishing the radii of the dentinal tubules. The dentin/pulp circulation and mineral defense system remains functionally intact, flowing, and even improved, which is important for the long term health and longevity of the dentition. It may be helped by the nitrate ion, since nitrate salts tend to increase circulation by being converted to nitric oxide. This is very important for long term vitality and longevity of the dentition as the dentin/pulp's afferent/efferent circulatory system is an extension of the pulp and its long term health is dependent on its remaining functional and flowing. It serves to replenish the dentin's mineral loss and as a barrier to combat the penetration of noxious substances and bacteria as well as a warning system for untoward changes that could make the pulp unhealthy. It may help also to accommodate for barometric and atmospheric changes such as is seen with deep sea diving, or air and space travel.

It takes usually 2–4 weeks for the potassium ions to penetrate through the structures described above, and into the pulp surrounding the nerves in sufficient numbers to desensitize a hypersensitive tooth. The addition of osmotic agent to compositions containing potassium increases the flow of potassium ions, nitrate ions, and fluoride through the dentin, quickly reaching the pulp in sufficient quantities to effect more complete, more rapid, and more lasting desensitization of supersensitive teeth.

Suitable potassium containing compounds include potassium bicarbonate, potassium biphthalate, potassium bromide, potassium chromate, potassium dichromate, potassium sulfate, potassium chromium sulfate, potassium thiocyanate, potassium bitartrate, potassium alum, potassium bromate, potassium fluoride, potassium hydrogen sulfate, potassium iodate, potassium tartrate, and other potassium compounds. Preferred potassium sources include potassium nitrate, potassium acetate, potassium chloride, potassium citrate, potassium phosphate, potassium carbonate, and other potassium compounds. Potassium nitrate is especially preferred because it can penetrate membranes readily, the nitrate yields nitric oxide, a blood vessel dilator, and it clinically works well to desensitize teeth.

Potassium is also known to be useful to treat ulcerative lesions of an oral and dermatologic nature. The present compositions containing potassium have been found to reduce or eliminate the pain associated with ulcers, especially aphthous ulcers, as well as herpes and Herpes Labialis. Some of the oral ulcerative lesions are acute necrotizing ulcerative gingivitis (ANUG), bullous ulcers, aphthous and herpetic lesions, traumatic ulcers, pemphigus, AIDS related ulcers, bullous Lichen Planus, oral shingles and others. Many of these ulcers are oral manifestations of dermatologic illnesses. Aphthous (Behcets), traumatic ulcers, Lichen Planus, Pemphigus, Lupus, are some of these diseases. Another of these ulcerative oral ulcers are seen as a sequelae to chemotherapy and radiation therapy. Shingles often exhibits dermatologic ulcers.

In both labial herpes and shingles the potassium ion if it was to help this condition would have to penetrate the skin and surround the involved nerve thus changing the nerve's threshold potential from about −80 to −90 millivolts to a zero or positive value. Potassium gels without dimethyl isosorbide are moderately helpful. A potassium nitrate gel with DMI increases the amount and speed of penetration of the ionic potassium. A high gradient of potassium is able to surround the nerves (central nervous system nerves and automatic system nerves) changing the threshold potential and preventing an action potential from taking place, and initiating pain or/and failing to allow the automatic nerves to signal for an inflammatory response. This makes the nerve unable to conduct an impulse thus eliminating the pain of these disease entities and hastening healing. For the treatment of ulcers, viscous preparations such as creams or gels are preferable because when applied liberally to the ulcers, they remain on the lesions and continually feed potassium into them, which reduces pain and hastens healing by reducing the inflammatory response. Suitable potassium containing compounds include those previously mentioned.

In one embodiment of the present composition, the active agent may be a topical corticosteroid. Topical corticosteroids may be absorbed from normal intact skin. When combined with DMI, the absorption of topical corticosteroids by the lesion is improved. As topical corticosteroids are absorbed through the skin, they enter pharmokinetic pathways similar to systemically administered corticosteroids. Topical corticosteroids are generally used for the treatment of swelling, inflammation, itching, and combinations thereof. Thus, topical corticosteroids are effective in the treatment of corticosteroid-responsive dermatoses primarily because of the anti-inflammatory, antipruritic and vasoconstrictive actions. Such symptoms may be caused by any number of skin conditions including eczema, dermatitis, rashes, insect bites, poison ivy, poison sumac, soaps, detergents, cosmetics, jewelry, Seborrheic Dermatitis, psoriasis, external anal and genital itching.

The extent of percutaneous absorption of topical corticosteroids is determined by many factors including the delivery vehicle, the integrity of the epidermal barrier, and the use of occlusive dressings. Inflammation and/or other disease processes in the skin may increase percutaneous absorption. Occlusive dressings substantially increase the percutaneous absorption of topical corticosteroids. Examples of topical corticosteroids include betamethasone, clobetasol, diisopropionate, dipropionate, hydrocortisone, propionate, and combinations thereof.

A preferred composition includes the topical corticosteroid betamethasone an active agent. The composition may be effective for treating, among other things, psoriasis, as betamethasone is often used to reduce inflammation of the skin of subjects with psoriasis. Psoriasis may be characterized by increased cell proliferation and increased skin thickening. The skin of subjects with psoriasis acts as a barrier to the absorption of corticosteroids and even percutaneous absorptive medications do not have the ability to fully penetrate to and below the basal membranes to reduce or arrest the proliferation and skin thickening seen in conditions such as psoriasis. The addition of osmotic agent to corticosteroids (or vitamin D) used to treat psoriasis enhances the absorption amount and penetration depth of the corticosteroid into the very proliferative skin layers of the psoriatic skin lesions, increasing the anti-inflammatory effect of the corticosteroid.

In another embodiment of the present composition, the active agent may be an anti-inflammatory drug. The osmotic agent enhances the passage of various molecules through the skin to the underlying tissues. One preferred embodiment of a composition includes the non-steroidal anti-inflammatory drug (NSAID), and vioxx, and the like which is an effective oral therapy for pain and inflammatory conditions. Such topical compositions, vioxx, and others may provide distinct advantages compared to oral usage. Thus, arthritis and other painful, inflammatory conditions may be treated while eliminating many of the safety issues associated with the oral use.

In another embodiment of the present composition, the active agent may be an anti-viral substances such as acetosalicylic acid, which is commonly used for the removal of warts. Osmotic agent increases the penetration and absorption of the acetosalicylic acid into and through the wart(s) thickness increasing the effectiveness of the active agent. The composition improves the penetration of the acetosalicylic acid into the basal layers of the wart to achieve increased effectiveness and efficacy of the active agent. Thus, healing of the wart lesions take place more quickly and completely than the preparation containing only acetosalicylic acid as an active agent. The composition may be effective for the treatment of all types of warts.

Other embodiments of the present composition may include anti-fungal substances such as amorolfine, ciclopirox, oxiconazole, and nystatin which are typically used to treat fungal infections of the nail (onychomycoses), which can occur in, around, or under the nail plate. Such infections are common and are reported in 2% to 14% of the population, but the actual incidence is probably much higher. The microorganisms involved are usually molds such as trichophyton rubrum, or yeasts, such as candida. Clinical investigations have demonstrated that it is feasible to treat fungal infections of the nail through the topical delivery of these antifungal agents. However, onset of visible cure is slow, treatment is usually long-term, and re-infection often occurs. The lack of a rapid visible onset of cure is a major reason for lack of patient compliance during therapy. By combining such substances with osmotic agent, the rate and extent of delivery of the aforementioned active agents through the nail plate to the nail bed is increased. Thus, therapeutically effective levels of the antifungal active agent within and below the nail are rapidly achieved, increasing the onset of the visible cure of fungal infections of nails.

In another embodiment of the composition the active agent may be a caries fighting substance. Most commercial dentifrices contain at least one caries fighting substance. "Dentifrice," as used herein, means a powder, paste, gel, or liquid for cleaning the teeth. Osmotic agent increases the penetration of caries fighting substances into tooth matter (enamel and dentin). For example, osmotic agent enhances the penetration of the fluoride ion into the tooth enamel and the 30,000–59,000/mm$^2$ dentinal tubules by with brushing with a dentifrice that contains fluoride and osmotic agent. The resistance of enamel and dentin to fluoride penetration is overcome and the fluoride ions penetrate in larger quantities and penetrate the tubular system in greater numbers enhancing the ability of fluoride to be a caries (including root caries) fighter. This is of major importance as fluoride is a major element involved in caries prevention, and when its effectiveness is enhanced and improved the battle against caries becomes more successful.

Suitable sources of fluoride include stannous fluoride, sodium fluoride, sodium monofluorophosphate, potassium fluoride, and the like. However, any source of fluoride may be used, as they all result in the release of fluoride ions into the saliva.

Potassium from any of the previously mentioned sources and fluoride from any of the previously mentioned sources may be incorporated into chewing gums and chewed to supply potassium ions for desensitizing/anesthetizing, as disclosed in U.S. patent application Ser. No. 5,522,726, to treat ulcers, and to fight caries with fluoride ions to the saliva and into tooth structure. Osmotic agent may also be combined with the chewing gums to enhance the penetration of such substances into the ulcers and tooth enamel and dentin (dentinal tubules), resulting in improved desensitization, protection from caries, or both. Upon being chewed, such a chewing gum releases the desensitizers directly into the saliva, allowing the active agents to enter the ulcers and the dentinal tubules and pass into the pulp. Such chewing gums also release the caries fighting substances directly into the saliva and then into tooth structure to prevent tooth decay. This effectively increases the desensitizing effect of potassium and allows the method of these ingredients being incorporated into chewing gum to be very effective for fighting caries and treating dentinal hypersensitivity (pain from thermal (hot, cold) chemical (sweet, sour, salt, acid etc.), and tactile (touch, brushing).

In another embodiment, the active agent may be a formulation for the treatment of erectile dysfunction, such as alprostadil. In the present embodiment, the composition is preferably formulated as a cream or ointment, and is applied locally on the glans (the head) of the penis. Thus, the side effects of delivery by injection or orally (e.g. with Viagra), such as heart attacks, possibly hitting a blood vessel during injection, and hematoma may be avoided. This approach to the treatment of impotence has important advantages.

The present invention will be further illustrated by the following examples, which are intended to be illustrative in nature and are not to be considered as limiting the scope of the invention.

WORKING EXAMPLES

The following examples were performed to evaluate the effectiveness of osmotic agents, (e.g., DMI) for enhancing the therapeutic effectiveness of a various active agents.

Example 1

Two compositions were formed, one containing DMI, and betamethasone, and the other containing hydrocortisone and DMI About 20–50 drops of DMI was added to 35 grams of Diprolene cream (augmented betamethasone), which is a commercially available cream containing about 0.05% betamethasone as well as 1% hydrocortisone cream.

The composition was used by a subject with psoriatic lesions of a rather extensive nature on the left and right elbows, right dorsal metacarpal (knuckle), and legs and buttocks. The left elbow had multiple markedly raised, red, hyperkeratotic lesions ranging from a 4 inch area to one-half inches. The knuckle had a circular lesion of about one inch long by ½ inch wide.

The lesions were previously treated over a 30+ year period using Diprolene cream two to four times daily. The Diprolene cream did not heal the psoriatic lesions, but it did keep them from exacerbating out of control.

The composition was applied directly to the aforementioned-mentioned psoriatic lesions 3–4 times per day. Within a week, the psoriatic lesions began to shrink, flatten, and became less red and raised. The hyperkeratotic character lessened. The lesions began to regress, fade, and shrink and were about 45–60% healed within about one week.

Treatment was continued for about 30 days. After 30 days, the lesions were improved, being smaller and flatter, but they failed to completely disappear.

Example 2

A composition for the treatment of pain was formed.

About 1–60 drops of osmotic agent were added to a commercial preparation containing 1% hydrocortisone. A male subject having an exquisitely painful ankle applied the composition directly to his ankle. The subject suffered from fasciitis and felt pain when walking.

Within five minutes after application of the composition, the subject's pain was reduced by about 80%. The subject was able to touch his ankle without as much pain and was able to walk with better vigor.

The DMI apparently synergized the hydrocortisone to penetrate to the source of the pain and diminished the pain by its anti-inflammatory action. The DMI enhanced the penetration of hydrocortisone into the affected areas, which could not be fully penetrated by the surface cortisone without DMI.

Example 3

A mixture of an osmotic agent and the topical corticosteroid betamethasone was prepared.

A patient having classically damaged nails from a fungal infection applied the composition directly to the nails and nail beds 4 times per day for a period of four months.

At the end of the four month period, the classically damaged nails were moderately improved, but the nails were not replaced with healthy new nails.

Example 4

A composition for the treatment of warts was formed.

DMI was combined with a commercial preparation containing acetosalicylic acid which was used to treat warts (plantar, palmar, and other dermatological warts).

The resulting composition is shown below in Table 1.

TABLE 1

| Function | Compound | Wt % |
| --- | --- | --- |
| Active Agent | Salicylic acid | 17.0 |
| Osmotic Agent | DMI | 3.0 |
| | alcohol | |
| | camphor | |
| | castor oil | |
| | colloidon 63/6 ether | |
| | ethylcellulose | |
| | hypophosphorous acid | |
| | menthol | |
| | Polporbate 80 | |

The composition increased the absorption and penetration of the acetosalicylic acid into the wart lesions, providing faster removal.

Example 5

A composition for the treatment of Herpes virus was formed by adding about 35–50 drops of osmotic agent to a gel preparation containing about 30 grams of potassium nitrate, about 17 grams of hydroxyethylcellulose, and about 28.35 grams of water.

Example 5A

Several subjects with Herpetic lip lesions applied the composition directly to the lesions three to four times per day. Herpetic lip lesions usually require about two to four weeks to heal.

The pain associated with the lesions was quickly alleviated, and pain relief remained for several hours without the need for a second application. Subjects were able to eat and speak comfortably. In all cases treated healing was reduced to about one week. In several cases when the subjects felt the lesions developing and immediately applied the gel, the lesions failed to form.

Thus, the composition provided good to excellent comfort and reduced healing time to at least one half the usual healing time.

Example 5B

Several subjects with shingles applied the composition directly to the Shingles lesions. Shingles is a condition which follows a single nerve. Shingles is usually a protracted and difficult to heal disease characterized by very painful lesions.

The subjects experienced good to excellent pain relief from the lesions when the composition was applied three to four to five times per day. In addition, healing of the lesions was hastened.

Example 6

A commercially available dentifrice was combined with DMI to provide the following composition:

TABLE 2

| Material | Wt % |
|---|---|
| Glycerine | 12.55 |
| Sodium Carboxymethyl Cellulose | 0.92 |
| Xantham Gum | 0.38 |
| Sodium Saccharin | 0.23 |
| Methylparaben | 0.06 |
| Propylparaben | 0.02 |
| Sorbitol Solution (70% w/v) | 9.00 |
| Potassium Nitrate | 5.00 |
| Sodium Laurel Sulfate | 2.10 |
| Colloidal Silica | 1.00 |
| Calcium Carbonate | 30.00 |
| Flavoring | 1.35 |
| Sodium Monflouroposphate | 0.81 |
| DMI | 2–50 drops/ounce |

I used this formula with six patients with 10 moderate to severe hypersensitive teeth. I applied it to the hypersensitive teeth in the office and gave some to the patients to apply at home. Two patients with 3 teeth had immediate relief as a result of the office application. The other four patients with 7 hypersensitive teeth brushed their teeth three times per day for at least a minute for each brushing, and the teeth all returned to normal within two to four days. All six patients (10 teeth) remained free of pain for three months of the study.

Example 7

A composition for the treatment of hypersensitive teeth, ulcers (oral and dermatologic), and herpetic lesions was formed as shown below in Table 4.

TABLE 3

| Function | Compound | Wt % |
|---|---|---|
| Base Gel | Glycerol | 60%–75% by wt. |
| Active Agent | potassium (from potassium nitrate) | from ½% wt % to about 35 wt % (Saturation) |
| Osmotic Agent | DMI | ½%–40% by wt. |

Example 8

Several compositions for the treatment of oral and dermatological ulcers were formed. The active agents were various potassium compounds, which have been found effective sources of potassium for the treatment of oral and dermatological ulcers. The concentrations of the various ingredients may be adjusted with commensurate adjustment of water to attain the desired percentage of these ingredients.

Example 8A

A composition for the treatment of oral and dermatological ulcers was formed as shown below in Table 5. The active agent was potassium nitrate, from a potassium nitrate source.

TABLE 4

| Function | Compound | Wt % |
|---|---|---|
| Solvent | Water | 86.5 |
| Active Agent | Potassium, from potassium nitrate | 11.5 |
| Osmotic Agent | DMI | ½%–40% by wt. |
| Thickener | Hydroxyethyl cellulose | 1.8 |
| Colorant | | 1.0 |

Example 8B

A composition for the treatment of oral and dermatological ulcers was formed as shown below in Table 6. The active agent was potassium, from a potassium chloride source.

TABLE 5

| Function | Compound | Wt % |
|---|---|---|
| Solvent | Water | 77.2 |
| Active Agent | potassium, from potassium chloride | 21.0 |
| Osmotic Agent | DMI | 0.5–40 |
| Thickener | Hydroxyethyl cellulose | 1.8 |
| Colorant | | 0.1–0.2 |

Example 8C

A composition for the treatment of oral and dermatological ulcers was formed as shown below in Table 7. The active agent was potassium, from a potassium acetate source.

TABLE 6

| Function | Compound | Wt % |
|---|---|---|
| Solvent | Water | 30.4 |
| Active Agent | Potassium acetate | 11.5 |
| Osmotic Agent | DMI | 0.5–35 |
| Thickener | Hydroxyethyl cellulose | 0.1–0.2 |
| Colorant | | 0.1–0.2 |

The potassium acetate can be altered from ½% to saturation in the same manner as with DMI and water.

Example 8C

A composition for the treatment of oral and dermatological ulcers was formed as shown below in Table 8. The active agent was potassium, from a potassium acetate source.

TABLE 7

| Function | Compound | Wt % |
|---|---|---|
| Solvent | Water | 30.3 |
| Source of Potassium | Potassium acetate | 67.3 |

TABLE 7-continued

| Function | Compound | Wt % |
| --- | --- | --- |
| Osmotic Agent | DMI | 0.5–50 |
| Thickener | Hydroxyethyl cellulose | 1.8 |
| Colorant | | 0.1–0.2 |
| | Titanium Dioxide | 0.6 |

Example 9C

A composition for the treatment of oral and dermatological ulcers was formed as shown below in Table 8. The active agent was potassium, from a potassium acetate source.

TABLE 8

| Function | Compound | Wt % |
| --- | --- | --- |
| Solvent | Water | 30.3 |
| Source of Active Agent | Potassium acetate | 67.3 |
| Osmotic Agent | DMI | 0.5–50 |
| Thickener | Hydroxyethyl cellulose | 1.8 |
| Colorant | | 0.1–0.2 |
| | Titanium Dioxide | 0.6 |
| Thickener | Methyl Cellulose | |

Example 10

A chewing gum for the prevention of caries and/or the desensitization of sensitive teeth was formed as shown below in Table 9.

TABLE 9

| Function | Material |
| --- | --- |
| Base | Gum Base |
| Active Agent | Desensitizer, any source of Potassium |
| Sweetener | Sugar, Aspartame, Saccharin |
| Flavoring | Any |
| Caries Fighter | Fluoride |
| Osmotic Agent | DMI |

Example 11

Several compositions for the treatment of tooth sensitivity were prepared by adding from one (1) to forty (40) drops of osmotic agent to a variety commercially available dentifrices, per ounce of dentifrice, as shown below in Table 10. The dentifrice and DMI were mixed thoroughly. Each dentifrice contained at least 5% potassium nitrate, as well as various amounts of humectants, surfactants, fluorides, abrasives, and/or binders. The osmotic agent combined well with the ingredients used in commercially sold dentifrices.

TABLE 10

| Dentifrice | DMI |
| --- | --- |
| Sensodyne | 1–40 drops |
| Aquafresh Sensitive | 1–40 drops |
| Crest Sensitive | 1–40 drops |
| Oral B Sensitive | 1–40 drops |
| Butler Sensitive | 1–40 drops |

Example 12

A composition containing about 12 drops of osmotic agent per ounce of Sensodyne (5% Potassium nitrate/0.24% NaF) was formed as in the previous Example.

The composition was applied to the hypersensitive teeth of 17 patients (48 teeth). Two ounces of the dentifrice was given to each patient for home self-treatment. They were told to brush their teeth for at least one minute, then to rinse out and apply a dab of the toothpaste to the sensitive teeth and leave it there.

I also added 12 drops of DMI to a 5% Potassium nitrate gel with a 0.24% NaF and aqueous hydroxethylcellulose. I applied the gel with a Q-tip to 19 patients' sensitive teeth (55) in the office, and they were given a 2-ounce bottle of gel for home application by brushing it onto their teeth with a toothbrush or applying it to the sensitive teeth with a Q-tip. They were told to leave it in place for one to two minutes, rinse with water and then to reapply the gel and leave it in place. They were to do this three times a day.

Seventeen patients with 48 hypersensitive teeth were given a dentifrice containing 5% potassium nitrate/0.24% sodium fluoride and 12 drops DMI per ounce of toothpaste for home self treatment. Using this altered Sensodyne dentifrice two patients with four sensitive teeth (moderate/severe supersensitivity) were free of pain immediately as a result only of applying the tooth paste to the sensitive teeth in the office setting. Seven patients with 12 hypersensitive teeth achieved normalcy, being free of pain within two days of office application and self-treatment, and the remaining seven patients (32 hypersensitive teeth) became free of pain and normal within three to four days. With 17 patients using the dentifrice, the degree of pain relief continued to improve for hours between applications of the dentifrice, indicating that the tooth continued to desensitize following the toothpaste's application.

Similar results were encountered with the use of the gel containing 5% Potassium nitrate/0.24% NaF and 12 drops of DMI per ounce of gel. Five patients (eleven hypersensitive teeth) had immediate relief and another with two hypersensitive teeth had notable pain reduction with an office gel application (going from severe pain to slight pain), and with two self applications of gel during the same day, the teeth became normal. All of the 19 patients (55 hypersensitive teeth) were normal within 2–4 days of treatment. The gel and toothpaste appeared to be equally effective with the patients all experiencing rapid (even immediate in some cases) pain relief from their hypersensitive teeth. The resultant comfort was profound, complete, more rapid, and lasting than with the use of 5% potassium nitrate dentifrices or gels without DMI.

DMI overcomes the resistance factors of dentin/pulp by enhancing potassium ion penetration through the dentin/pulp barriers. Genuine patient comfort was achieved, often within a couple of days and in all instances by four days of desensitizer usage. The patients were given only two ounces of dentifrice or gel, and they reported no recurrences in up to three months follow-up. No untoward or deleterious reactions were seen in the oral tissues or the teeth. There were no visible red or white lesions, irritations, ulcerations, or constitutional effects observed or reported. Its effectiveness, amazingly, increases between applications of the desensitizing dentifrice or gel, as it continues to more profoundly desensitize the teeth hours after its application to the teeth, which is very important for the health and longevity of the dentition. DMI increases the efficiency and therapeutic effectiveness of potassium while allowing the tooth with its pulp and extended dentinal tubular circulatory defense system to remain intact and fully functional, which may allow the continued return to normalcy between the applications of the desensitizing dentifrice or gel.

DMI/$KNO_3$ desensitizes hypersensitive teeth more efficaciously than $KNO_3$ alone. DMI readily penetrates the dentinal tubule orifices and travels rapidly through the pulpal tissues. DMI enhances $KNO_3$'s effectiveness, causing it to work by a different mode of action than occurs when used alone. $KNO_3$ used in a desensitizing dentifrice or other preparation without DMI also travels through the dentinal tubules, but at a slower rate. It causes the pulpal nerves to depolarize by bathing them with potassium ions. It changes the minus 85 millivolt resting threshold potential to a zero or a positive value preventing an action potential from forming. This inhibits nerve conductance and pain emission. In this way it desensitizes hypersensitive teeth.

The addition of DMI to $KNO_3$ dynamically potentiates the desensitizing effects of $KNO_3$ due to its strong osmotic qualities. As it travels towards the pulp via the dentinal tubule conduit it overcomes the resistant factors of the dentin/pulp barriers. DMI helps $KNO_3$ to more rapidly reach the all important pulpal nerves, blood vessels and embryonic connective tissues. It overcomes the tubular constrictions, irregularities, man-made tubular obliterations, dentinal sclerosis, odontoblast processes, fluid with contained minerals and immunoglobulins, tubule contained bacteria, antibiotics, antimicrobial agents, odontoblasts, odontoblast junctions (tight, intermediate and gap), and intercellular bridges that join cells. These structures restrict and slow the penetration of potassium into pulpal tissues. As $DMI/KNO_3$ advances through the dentinal tubules it encounters the structures cited. Due to DMI's osmotic properties, it opens intercellular spaces between cells as well as space through cells. The intercellular bridges connecting cells (such as odontoblasts) serve as permeability barriers. DMI raises the osmotic pressure of fluid surrounding cells and other membranous structures shrinking them in size. The fluid containing $KNO_3/DMI$ flows through the widened bridge spaces, junctions, and enlarged openings between the shrunken osteoblasts processes and osteoblasts enhancing and enabling potassium dentin/pulp permeability. The $KNO_3/DMI$ fluid flows more rapidly and easily through these newly created spaces to reach pulpal nerves and blood vessels. In the same way as described pulpal nerves lose water and shrink significantly due to the increased osmotic pressure caused by the surrounding solution. When cells and membranous structures are caused to shrink osmotically by DMI, potassium located outside the nerve's membrane, as well as potassium from the high potassium gradient obtained from the $KNO_3$/osmotic agent desensitizer, flows rapidly into these nerve cells in quantity. Osmotic cell shrinkage is a strong stimulus for the uptake of potassium. As the captured cellular potassium leaves the inside of nerves it escapes leaving strongly negative hyperpolarized nerves that can not form an action potential. This dynamic process inhibits pain production and nerve conduction. Desensitization of hypersensitive teeth is accomplished in this way. It takes place faster, more completely and lasts longer than with just the use of $KNO_3$ to bathe teeth. This is due to the way DMI works osmotically. The teeth desensitize faster than with $KNO_3$ alone as the $KNO_3/DMI$ penetrate through the dentinal tubules at a more rapid rate for the reasons described. However, a major reason for the increased speed of tooth desensitization is that hyperpolarization is a result of DMI's osmotic ability to cause cell shrinkage. It takes place immediately while $KNO_3$ depolarizes the nerve and this takes longer to accomplish. The reason for this is that water moves faster than potassium. $KNO_3/DMI$ accomplishes desensitization without obliterating or diminishing the radius of the dentinal tubules. The dentin/pulp circulation and natural dentin and pulp defense system remains functionally intact, flowing, and even improved. It may be helped by the nitrate ion, since nitrate salts tend to increase circulation by being converted to nitric oxide. This is very important for long term vitality and longevity of the dentition as the dentin/pulp's afferent/efferent circulatory system is an extension of the pulp and its long term health is dependent on its remaining functional and flowing. It serves to replenish mineral loss and as a barrier to combat the penetration of noxious substances and bacteria as well as a warning system for untoward changes that could make the pulp unhealthy. It may help also to accommodate for barometric and atmospheric changes such as is seen with deep sea diving, or air and space travel.

The osmotic agent DMI works with the active agent to disturb the functions of the nerve cell simultaneously depolarizing and hyperpolarizing it. These agents antagonize the recovery process to the resting potential. Potassium positioned on the outside of the nerve keeps it depolarized. This slows the escape of the potassium held within the nerve's membrane and makes it more difficult for the nerve to recover volume after shrinking. A lot of potassium outside the nerve keeps the cell shrunken, and if the nerve is shrunken, it is not going to work well. This keeps the nerves inactive longer. Desensitization of hypersensitive teeth by the combinations of DMI and potassium nitrate is more effective and efficient than when $KNO_3$ is used alone. They work to desensitize hypersensitive teeth at a higher, quicker, more profound and lasting level.

Example 13

A composition for the treatment of calluses and rough skin was formed by combining osmotic agent and petroleum jelly. The composition was applied to calluses on sole and heel areas of the feet of a subject that had existed for many years. The composition was applied twice daily. White socks were placed on the feet of the subject after applying the composition at night. An immediate improvement was seen. The callus had markedly diminished and softened and an obvious improvement occurred. The more the composition was applied, the more the calluses were reduced and the smoother and softer the feet became. The soft calluses were also more easily trimmed once they had softened. The composition was surprisingly effective for areas of hyperkeratosis (calluses) on the hands and feet or other frictional surfaces. The DMI enhanced the beneficial effects of petroleum jelly by enhancing its penetration within the deeper skin layers.

Example 14

A composition of DMI and Calcipotriene (a synthetic Vitamin $D_3$ derivative) was formed. Calcipotriene is contained in Dovonex, which is an ointment for topical dermatological use. The composition was formed by dissolving the DMI in petrolatum, followed by adding Dovonex ointment to the DMI/Dovonex mixture. DMI does not directly dissolve in Dovonex. DMI remains in solution with Dovonex when mixed in this manner.

Chemically, Calcipotriene is (5Z, 7E, 22E, 24S)-24 cyclopropyl-9, 10-secochola-5, 7 (19) 22 tetraene 1X, 3B, 24 triol with the emperical formula $C_{27}H_{40}O_3$, and a molecular weight of 412.6. Calcipotriene is a white or off-white crystalline substance.

Dovonex contains Calcipotriene 50 mg/g in an ointment base of dibasic sodium phosphate, edtate disodium, mineral glycerin, oil, petrolatum, propylene glycol, tocopherol, and water.

In humans, the natural supply of Vitamin D depends mainly on exposure to the ultraviolet rays of the sun for conversion of 7-dehydrocholesterol to Vitamin D (cholecalciferol) in the skin. Calcipotriene is a synthetic analog of Vitamin $D_3$. Clinical studies with radiolabeled Calcipotriene ointment indicate that approximately 6% of the applied dose of Calcipotriene is absorbed systemically when the ointment is applied topically to psoriasis plaques or 5% active when applied to normal skin, and much of the absorbed active is converted to inactive metabolites within 24 hours of application.

Vitamin D and the metabolites are transported in the blood, bound to specific plasma proteins. The active form of the vitamin, 1, 25-dihryoxy vitamin $D_3$ (calcitrol) is known to be recycled via the liver and excreted in the bile. Calcipotriene metabolism following systemic uptake is rapid and occurs via a similar pathway to the natural hormone.

Adequate and well controlled trials of patients treated with Dovonex ointment (twice daily) have demonstrated improvement usually beginning after two weeks of therapy. This improvement continued with approximately 50% of patients showing at least marked improvement in the signs and symptoms of psoriasis after eight weeks of therapy, but only approximately 4% showed complete clearing.

Although the precise mechanism of Calcipotriene's antipsoriatic action is not understood, in vitro evidence suggest that Calcipotriene is roughly equipotent to the natural vitamin in its effects on proliferation and differentiation of a variety of cell types. Calcipotriene has also been shown in animal studies to be 100 to 200 times less potent in its effects on calcium utilization than the natural hormones.

Clinical studies with radiolabeled Calcipotriene solution indicate that less than 1% of the applied dose of Calcipotriene is absorbed through the scalp when the solution (2.0 ml) is applied topically to normal skin or psoriasis plaques (160 $cm^2$) for 12 hours and that much of the absorbed Calcipotriene is converted to inactive metabolites within 24 hours or application.

DMI, when added to Dovohex, enhances the beneficial effects of Calcipotriene, apparently increasing the absorption into and below the psoriasis plaques, causing them to start to soften and flatten overnight. By applying the DMI/Dovonex ointment twice a day, they continue to disappear. Within a week, the lesions are almost cleared; and with continued applications of the DMI/Dovonex ointment b.i.d. for a second week, or third week, complete clearing of the psoriasis plaques usually takes place with the skin appearing normal. The DMI enhances the Dovonex, causing this commercial preparation (prescription) to become an effective treatment for clearing psoriasis plaques.

The DMI/Dovonex composition was used on a male subject with seven psoriatic areas on his body which were calcitrant to all topical medications, including Dovonex, for 35 years. Using DMI/Dovonex b.i.d., in two weeks all seven areas were clear of psoriasis plaques. DMI/Calcipotriene in a vehicle (Dovonex) apparently inhibited undesirable proliferation of certain cells and abnormal cell differentiation far better than with Calcipotriene alone.

The composition was also applied to the male subject's psoriatic nails. It takes time for nails to grow, but the results (improvement) have been remarkable so far. In ten days of b.i.d. application of Dovonex/DMI gel application, the subject's nails have shown remarkable improvement.

Although particular embodiments of the invention have been described in detail for purposes of illustration, various changes and modifications may be made without departing from the scope and spirit of the invention. All combinations and permutations of the compositions and methods are available for practice in various applications as the need arises. For example, the compositions and methods of the invention may be applied to processes that are presently not practically feasible. Accordingly, the invention is not to be limited except as by the appended claims.

What is claimed is:

1. A method of decreasing the volume of a cell having a membrane and an electrical potential across the membrane that is substantially equal to a resting threshold potential, comprising the step of:

topically applying a composition containing an osmotic agent;

increasing the electrical potential across the cell membrane to a level greater than the resting threshold potential; and decreasing the electrical potential across the cell membrane to a level less than the resting threshold potential.

2. The method of claim 1, wherein the composition further includes an active agent.

3. The method of claim 2, wherein the osmotic agent is dimethyl isosorbide.

4. The method of claim 3, wherein the active agent is an anti-inflammatory compound.

5. The method of claim 3, wherein the active agent is a desensitizing agent.

6. The method of claim 3, wherein the active agent is a caries fighting substance.

7. The method of claim 3, wherein the active agent is a pain reliever.

8. The method of claim 3, wherein the active agent is a skin treatment.

9. The method of claim 1, wherein the active agent is calcipotriene.

10. The method of claim 4, wherein the anti-inflammatory agent is a topical corticosteroid.

11. The method of claim 10, wherein the topical corticosteroid is selected from the group consisting of clobetasol, propionate, hydrocortisone, betamethasone, diipropionate, and combinations thereof.

12. The method of claim 11, wherein the topical corticosteroid is betamethasone.

13. The method of claim 5, wherein the desensitizing agent is a source of potassium.

14. The method of claim 13, wherein the source of potassium is selected from the group consisting of potassium bicarbonate, potassium biphthalate, potassium bromide, potassium acetate, potassium chloride, potassium phosphate, potassium carbonate, potassium chromate, potassium dichromate, potassium sulfate, potassium chromium sulfate, potassium thiocyanate, potassium bitartrate, potassium alum, potassium bromate, potassium fluoride, potassium hydrogen sulfate, potassium iodate, potassium tartrate, and combinations thereof.

15. The method of claim 14, wherein the source of potassium is potassium nitrate.

16. The method of claim 6, wherein the caries fighting substance is selected from the group consisting of potassium, fluoride, and combinations thereof.

17. The method of claim 16, wherein the caries fighting substance is fluoride.

18. The method of claim 7, wherein the pain reliever is selected from the group consisting of vioxx, ibuprofen, acetaminophen, and combinations thereof.

19. The method of claim 8, wherein the skin treatment is selected from the group consisting of a moisturizer, a humectant, an exfoliant, and combinations thereof.

20. The method of claim 1, wherein the membrane is the membrane of a nerve cell.

21. The method of claim 1, wherein the membrane is the membrane of a tumor cell.

22. A therapeutic composition comprising dimethyl isosorbide and a desensitizing agent.

23. A therapeutic composition comprising dimethyl isosorbide and a caries fighting substance.

24. The therapeutic composition of claim 22, wherein the desensitizing agent is a source of potassium.

25. The therapeutic composition of claim 24, wherein the source of potassium is selected from the group consisting of potassium bicarbonate, potassium biphthalate, potassium acetate, potassium carbonate, potassium chloride, potassium phosphate, potassium bromide, potassium chromate, potassium dichromate, potassium sulfate, potassium chromium sulfate, potassium thiocyanate, potassium bitartrate, potassium alum, potassium bromate, potassium fluoride, potassium hydrogen sulfate, potassium iodate, potassium tartrate, and combinations thereof.

26. The therapeutic composition of claim 25, wherein the source of potassium is potassium nitrate.

27. The therapeutic composition of claim 23, wherein the caries fighting substance is selected from the group consisting of potassium, fluoride, and combinations thereof.

28. The therapeutic composition of claim 27, wherein the caries fighting substance is fluoride.

29. A therapeutic composition comprising dimethyl isosorbide and calcipotriene.

30. A therapeutic composition comprising dimethyl isosorbide and a pain reliever selected from the group consisting of vioxx, ibuprofen, acetaminophen, potassium containing compounds, and combinations thereof.

31. A method of relieving pain in a subject, comprising:
topically applying an effective amount of a composition containing dimethyl isosorbide and potassium to skin of a subject experiencing pain.

32. A method of treating psoriasis in a subject, comprising:
topically applying an effective amount of a composition containing dimethyl isosorbide and calcipotriene to skin of a subject effected by psoriasis.

33. A chewing gum or lozenge comprising a non-electrolytic osmotic agent and potassium.

34. A chewing gum or lozenge comprising potassium and dimethyl isosorbide.

35. The method of claim 7, wherein the pain killer is potassium nitrate.

* * * * *

UNITED STATES PATENT AND TRADEMARK OFFICE
CERTIFICATE OF CORRECTION

PATENT NO. : 6,524,623 B1  
APPLICATION NO. : 09/633424  
DATED : February 25, 2003  
INVENTOR(S) : Milton Hodosh It is certified that error appears in the above-identified patent and that said Letters Patent is hereby corrected as shown below:

Column 2, line 4, "varoety" should read --variety--.

Column 2, line 6, "ound" should read --found--.

Column 2, line 6, "tubles sometim" should read --tubules sometimes minimize or prevent--

Column 2, line 8, "cell" should read --cells--.

Column 2, line 9, "charging" should read --changing--.

Column 4, line 19, "The" should read --They--.

Column 4, line 31, "relive" should read --relieve--.

Column 9, line 8, "automatic" should read --autonomic--.

Column 9, line 10, "automatic" should read --autnomic--.

Column 19, line 27, "Dovohex" should read --Dovonex--.

Signed and Sealed this

Twentieth Day of February, 2007

JON W. DUDAS  
*Director of the United States Patent and Trademark Office*